United States Patent [19]
Detournay et al.

[11] Patent Number: 5,670,711
[45] Date of Patent: Sep. 23, 1997

[54] PORTABLE ROCK STRENGTH EVALUATION DEVICE

[75] Inventors: Emmanuel Detournay, Roseville; Andrew Drescher, New Brighton; David A. Hultman, Cambridge, all of Minn.

[73] Assignee: Regents of the University of Minnesota, Minneapolis, Minn.

[21] Appl. No.: 613,016

[22] Filed: Mar. 8, 1996

[51] Int. Cl.⁶ .................................................. G01N 3/00
[52] U.S. Cl. ........................... 73/84; 73/152.09; 73/866
[58] Field of Search ........................ 73/152.01, 152.08, 73/152.09, 152.11, 152.17, 78, 84, 866

[56] References Cited

U.S. PATENT DOCUMENTS

| | | | |
|---|---|---|---|
| 4,562,726 | 1/1986 | Barnaby | 73/38 |
| 5,216,917 | 6/1993 | Detournay | 73/151 |
| 5,323,648 | 6/1994 | Peltier et al. | 73/152.17 |
| 5,415,030 | 5/1995 | Jogi et al. | 73/152.03 |

FOREIGN PATENT DOCUMENTS 0 559 286 A1  8/1993  European Pat. Off. .

OTHER PUBLICATIONS

Emmanuel Detournay, Andrew Drescher, Paul Defourny and Dominique Fourmaintraux; "Assessment of rock strength properties from cutting tests: preliminary experimental evidence", *Colloquium Mundanum* 1995, pp. 1.1.12–1.1.22.

E. Detournay and P. Defourny; "A Phenomenological Model for the Drilling Action of Drag Bits", *Int. J. Rock Mech. Min. Sci. & Geomech. Abstr.*, vol. 29, No. 1, , 1992, pp. 13–22.

J.R. Almenara and E. Detournay; "Cutting experiments in sandstones with blunt PDC cutters", *Eurock '92 Thomas Telford London*, 1992, pp. 215–220.

*Primary Examiner*—George M. Dombroske
*Assistant Examiner*—Max H. Noori
*Attorney, Agent, or Firm*—Westman, Champlin & Kelly, P.A.

[57] ABSTRACT

A portable frame that includes a movable support for supporting a cutting tool used for engaging a rock sample, and upon relative movement between the rock sample and the cutter, the cutter will make a constant depth cut at a constant velocity. During the cut, the forces parallel to the direction of displacement and perpendicular to the direction are measured, and both cohesion and internal friction angle, which are parameters characterizing the rock strength, the internal friction angle, which is a true measure of the rock strength, can be determined.

9 Claims, 4 Drawing Sheets

PORTABLE ROCK STRENGTH EVALUATION DEVICE

BACKGROUND OF THE INVENTION

The present invention relates to a portable rock strength evaluation device for determining the internal friction angle and cohesion in rock samples, using a precisely made cutter that is moved relative to the rock sample at a constant depth while the forces on the cutter are measured. The cutter geometry is such that correct measurements of the rock friction angle can be made directly, so that rapid testing is achieved on site.

Various devices have been advanced for determining the internal friction angle of rocks, primarily in relation to determining drilling conditions in a bore hole.

Typical devices are shown in U.S. Pat. No. 5,216,917, which concerns a method of determining the drilling conditions associated with drilling of a bore hole through subterranean formations using a rotary drag bit by following specific procedures, the internal friction angle of the formation can be estimated.

European patent application 0 559 286 discloses a tool for measuring the mechanical properties of a formation through which a bore hole has been drilled, wherein the tool body is lowered into the bore hole and has pads mounted on movable arms which engage the surface of the bore hole. Each pad carries a cutter that is urged against the bore hole wall so as to cut into the formation. These cutters are monitored for determining the depth of cut made by the cutter and for determining the resistance of the rock to cutting. The tool is not suitable for use in connection with testing the strength of rock samples and requires substantial monitoring of the process in order to be reliable.

However, both of the above-identified publications contain substantial discussions of the forces on a rock cutter, and the resulting information that can be obtained from analyzing the forces. However, specifically, the cutters are envisioned to be wear in type cutters and not precision made cutters as used with the present portable device.

SUMMARY OF THE INVENTION

The present invention relates to a portable rock strength evaluation device for measuring mechanical properties of rock samples, quickly, and conveniently, and obtaining very accurately the internal friction angle of the rock. The invention also includes the use of a uniquely formed blunt cutter for cutting a precise and known constant depth in the rock sample as the sample and the cutter are moved relative to each other at constant speed so the forces occasioned by the relative movement and the cutting can be accurately measured. Sharp cutters will provide information on rock cohesion using the present portable device.

The cutter is preferably polycrystalline diamond compact material, and the blunt cutter is precisely formed so that the angle of the flat face that engages the rock sample as the cut is made is a true flat surface, and is machined or formed at a precise angle relative to the plane of travel of the edge of the cutter. The angle is such that when the cutter is held and there is relative movement, the rock is destroyed ahead of the cutter, and the rock crumbles and forms a powder so that a boundary layer of powder is formed under the lowest flat face and the surface of the rock after the cut. The formation of this powder boundary layer allows measurement of the rock friction angle directly.

The sides of the cutter are also tapered in a trapezoidal shape to minimize the frictional contact between the sides of the cutter and the rock sample.

The depth of cut is kept very small, so that the cutting test with a blunt cutter provides a direct measurement of the friction angle, based upon the vertical force (against the rock sample), that is, the force $F_n$, normal to the direction of relative movement or displacement of the cutter and the rock sample, and the horizontal cutting force, $F_s$ which is parallel to the direction of displacement.

Further, the sharpness of the cutter can be monitored by using the same measured forces. A constant that is developed by dividing the horizontal force $F_s$ into the vertical force $F_n$. If this ratio ($F_n/F_s$) is greater than the constant equal by the tangent of the cutter rake angle plus the interfacial friction angle on the cutting face by a predetermined amount, the cutter could be considered to be blunt.

The interpretation of the force measurements, in obtaining rock strength parameters is possible only if the mode of destruction of the rock is plastic. The present invention relates to use with sedimentary rocks, such as sandstones, limestones, shales, chalk and the like, and in rocks of this type, the rock destruction takes place for depths of cut typically smaller than 3 mm. The preferred depth of cut is much less than the maximum. Larger depths will cause chipping of the rock which is associated with a brittle mode of failure. Again, plastic failure is required, to develop the appropriate interpretation of forces, as well as to form the boundary layer of crushed or dust like rocks underneath the surface of the cutter adjacent the rock.

DETAILED DESCRIPTION OF THE PREFERRED EMBODIMENTS

A portable rock strength evaluation device indicated generally at 10 is made according to the present invention. It is a portable unit, for example having a height in the range of 12 plus inches, and a width about the same. The testing device frame 12 is made to be extremely rigid, so that the tests can be carried out in a reliable manner.

The frame 12 comprises a pair of heavy side plates 14, 14 that are spaced apart and are used to mount the components between them. The plates have suitable adjustable feet 15 thereon, for leveling and support.

Figure 3:
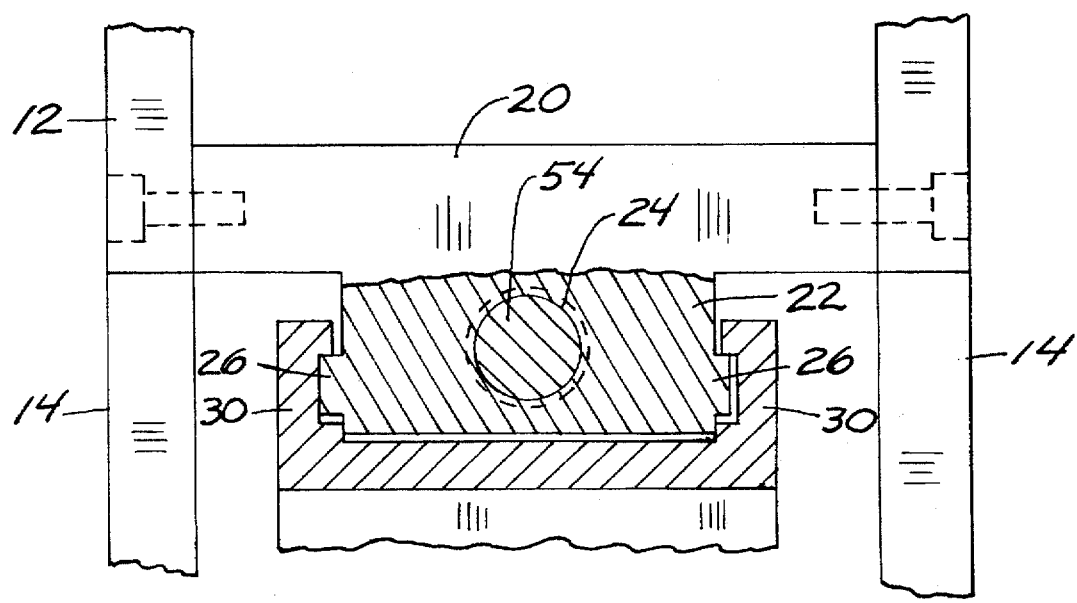
FIG. 3 is a sectional view taken as on line 3—3 in FIG. 2.

The evaluation device comprises two main components including a rock sample support assembly 16 and an adjustable cutter support assembly 18. The cutter support assembly 18 comprises a solid mounting block 20 that is bolted between the side plates 14, 14 or can be otherwise suitably rigidly attached. The block 20 as shown in FIG. 3 has a forwardly projecting mounting block or support 22, that is provided with a threaded bore 24, and male guides 26 on opposite side surfaces thereof. The block 22 movably and adjustably supports a cutter support 28. The cutter support 28 is a slide for a guideway assembly that has side members 30 with receptacles or guideway grooves that slidably receive the guides 26, so that the slide or cutter support 28 can move vertically along the guides 26 of the block 20.

The slide or cutter support 28 further has a forwardly projecting lug 32 that defines a recess below it. A strain gauge force transducer has one mounting 36 fixedly onto the lower side of lug 32 of slide 28. The transducer 36 is a commercially available unit and the lower side supports a flange 37 holding a depending cutter support lug 38 at the bottom side thereof. This construction can be modified if desired, but rigidity and minimizing deflection when the cutter supported thereon is under load is of importance. It can be seen that the side members 30 as well as side plates 14 are spaced apart a substantial distance to minimize the tendency to have deflections from torque exerted on a cutter assembly 40 which is shown supported on the lug 38.

Figure 4:
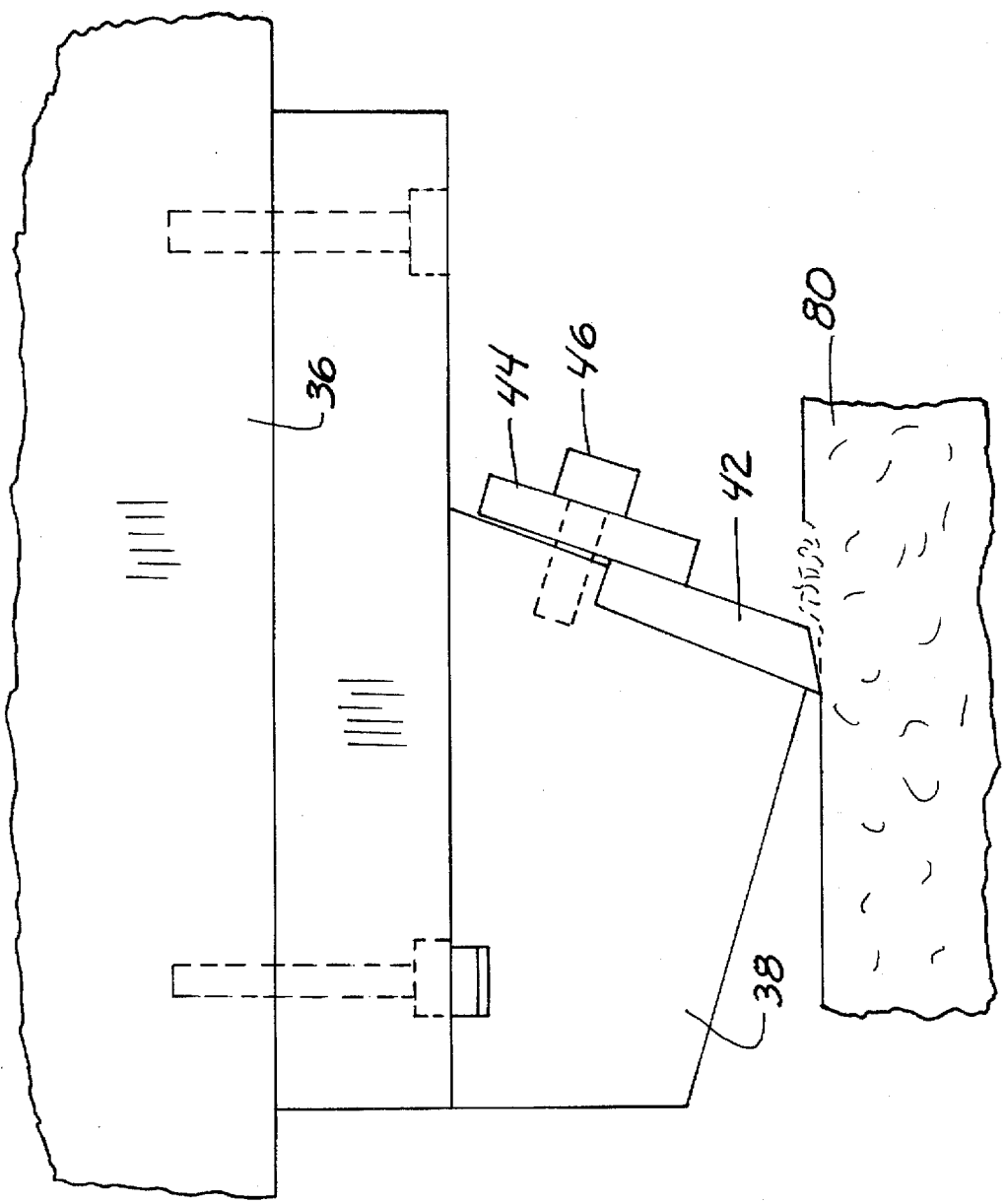
FIG. 4 is an enlarged side elevational view of a typical mounting for the cutter used with the device in FIG. 1.

As can be seen in FIG. 4, the cutter support lug 38 has a recess at its forward edge for receiving a cutter 42 that is held in a suitable clamp washer 44 with a capscrew 46 in a conventional manner. The loads on cutter lug 38 are measured parallel to the direction of displacement and also normal thereto. The transducer 36 is provided with strain gauge sensors that measure vertical forces ($F_n$), which is the force normal to the relative direction of displacement of a rock sample and cutter. Also strain gauges or other sensors are provided in transducer 36 and are oriented to measure the force parallel to the relative direction of movement or displacement of rock sample, or $F_s$. The transducer 36 is made by NK Engineering of Minnetonka, Minn. The forces are measured with little deflection.

The mounting block 18 has a rearwardly extending flange 52 thereon, and this flange rotatably mounts a micrometer or very fine adjustment screw 54 so that the screw will react loads in both directions. Suitably thrust washers 56 can be mounted on the opposite sides of the flange 52, and when the screw 54 is threaded into the threaded bore 24 of block 20 it will adjust the vertical height of the slide or cutter support 28 and thus the cutter assembly 40 relative to the rock sample support assembly 16.

Additionally, the slide or cutter support 28 can mount a depth of cut sensor illustrated schematically at 60 on its lower surface, the sensor 60 is aligned with the lower end of the cutter 42, and can be used for determining when the top surface of a rock sample is engaged, and then also determine what depth of cut is being made. This can be a laser type sensor or optical type displacement sensor or other non contact sensor that will provide necessary information.

The vertical position of the cutter 42 can also be determined by utilizing an LVDT sensor indicated at 62 to sense movement between the flange 52 and the block 20. Any deflections of the frame 12 under high loads can be compensated.

The rock support assembly 16 includes a main mounting block 70 which is fastened in a suitable manner between the side plates 14, 14 and this mounting block has an upper head portion 70A that forms a guideway, having guideway projections 72 on opposite sides thereof. A slide 74 has depending side members 76 that have mating receptacles, so that a very close fitting guideway is made for the slide 74. The slide 74, as shown, carries a rock sample cradle 78, mounted fixedly to the slide, and this cradle is adapted to mount a suitable rock sample shown schematically at 80, using known clamps 81. Two clamps at least would be used although only one is shown.

Figure 1:
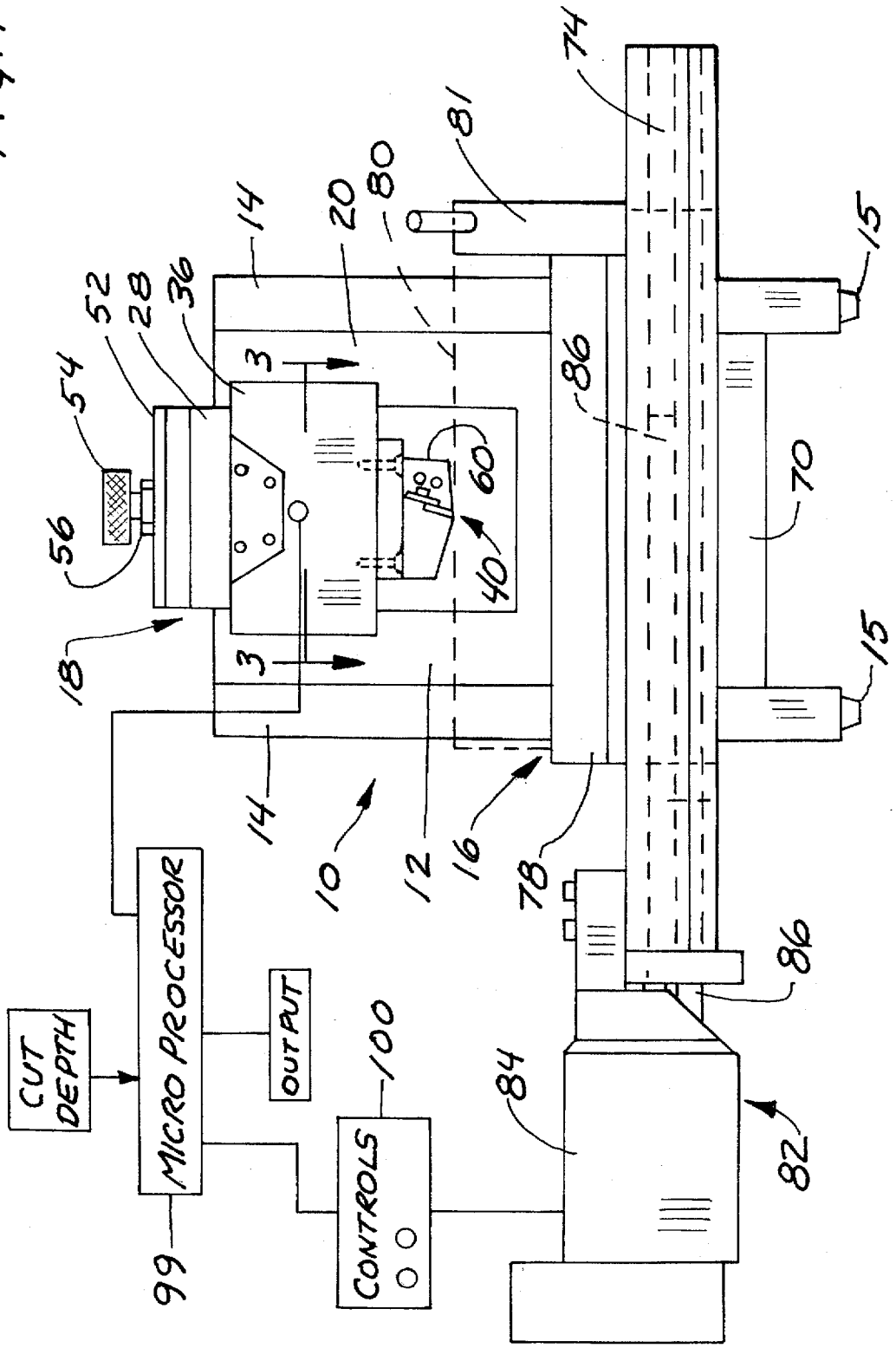
FIG. 1 is a side elevational view, part schematic of a portable rock testing device made according to the present invention.
Figure 2:
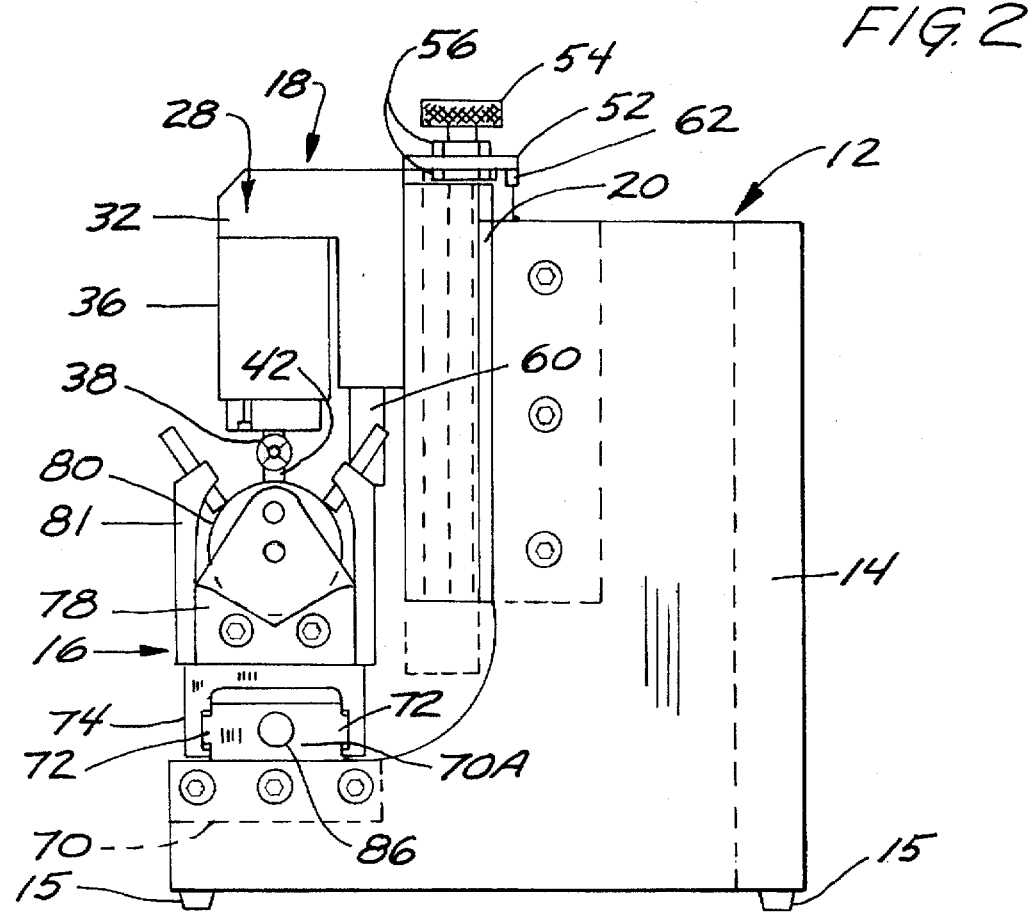
FIG. 2 is a front view thereof.

The position of the slide 74 along the guide 72 is controlled precisely with a screw drive, such as a very precise ball screw. The screw drive shown at 82 includes a drive motor 84, operating a screw 86 through conventional gear reduction, the screw is threaded into a longitudinal bore. The bore can be manufactured to accept the desired screw. The ball assembly 82 and the motor 84, as well as the drive arrangement for the screw 86 can be mounted onto the slide 74, as shown schematically in FIG. 1, and then when the screw is driven, the entire slide 74 and cradle 78 will move relative to the block 70A and the cutter a desired amount so that the rock sample 80 can be moved past the cutter when the proper depth of cut has been arranged.

Figure 5:
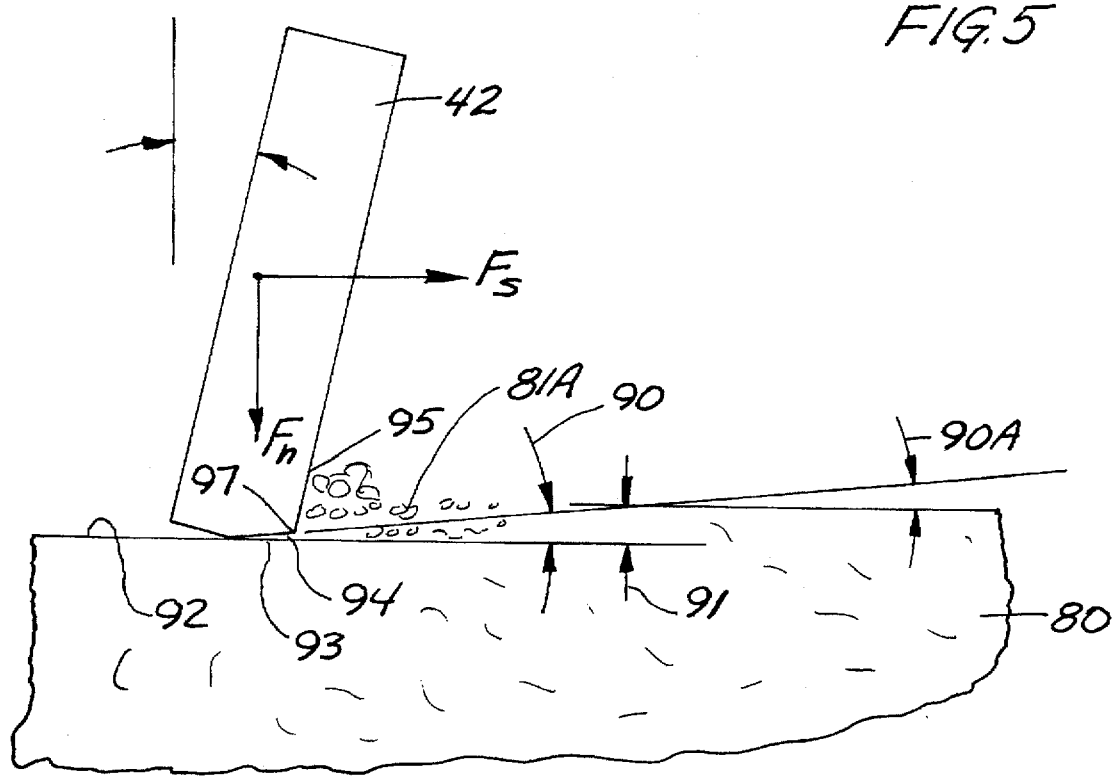
FIG. 5 is an enlarged part schematic view showing the action of the cutter of the present invention working on a typical rock sample.
Figure 6:
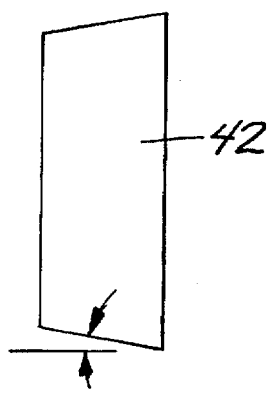
FIG. 6 is a top plan view of the cutter of FIG. 5.
Figure 7:
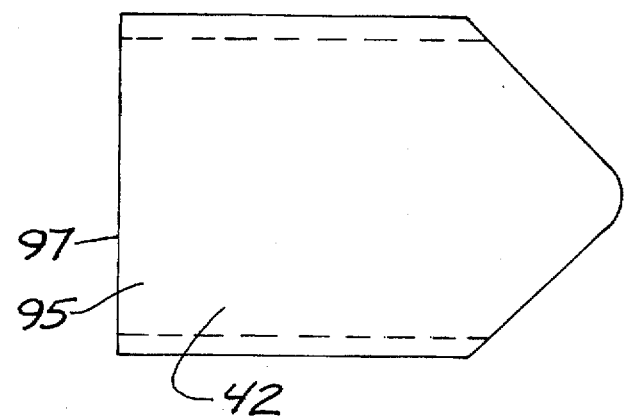
FIG. 7 is a front view of the cutter.

A typical cutter is shown in FIGS. 5, 6 and 7 as shown, this cutter 42 is formed with a flat face at the lower end that is cut precisely at 17° when made. The cutter holder 38 is made to hold the cutter at an angle of 15° from a line normal to the direction of travel, so that the cutter has a 2° upward incline relative to the rock sample 80, as shown in FIG. 5 at 90 and 90A.

Schematically shown in FIG. 5 is the region of the rock sample shown at 81A just immediately ahead of the cutting face 95 of cutter, which is where the rock is destroyed for the depth of cut indicated by the arrows 91. This destruction of the rock in the region 81A causes a crumbling and most of this crushed material will be dropped off the rock sample as the cut is made so that the cutter leaves a smooth surface shown at 92 behind the cutter 42 and underneath the flat face 93. The face 93 is inclined preferably 2° and no more than 4° from the plane of the cut shown by the line 92. A powder indicated at 94 is formed under this face due to the high vertical force that can be developed to form a boundary layer under the flat face.

To measure the rock friction angle, a two-face cutter 42 is used. One of the faces is the cutting face 95. The other face is the machined flat 93 which is inclined upwardly in the direction of relative motion of the cutter, and thus upwardly toward a leading edge 97, by a small angle (typically in the range of 1° to 4°). The small angle (shown exaggerated in FIG. 5) of upward inclination of the flat face ensures that a large vertical force is generated across the flat 93 onto the cut surface 92. This large force contributes to the development of the boundary layer of crushed rock which forms under the flat surface of the cutter. Formation of this boundary layer insures accurate measurement of the rock friction angle by analysis. Furthermore, the sides of the cutter are tapered as shown in FIG. 6 to minimize lateral frictional contact between the cutter and the rock as shown. The top of the cutter 42 is tapered as shown in FIG. 7. The width of the cut is defined by the length of the junction line 97 between cutting face 95 and flat face 93.

The controls of the vertical cutter adjustment permits precise adjustment of the depth of cut, which is maintained constant during a cutting test. The speed of movement between the cutter can be selected as desired and is maintained constant. A nominal speed of 1 cm/sec is normal, but other speeds can be selected. A constant speed of movement is needed for an accurate test.

Monitoring of the depth of cut also can be carried on. A laser system can be used in the machine to measure the actual depth of cut.

Direct measurement of the rock friction angle $\phi$ is accomplished by carrying out a cutting test with a blunt cutter 42, at very small depth of cut (preferably in the range of 0.05 to 0.1 mm, but the cut may be slightly more). The friction angle $\phi$ is then directly determined from $$\tan\phi = \frac{F_s}{F_n}$$

where $F_n$ is the vertical force, and $F_s$ the horizontal force measured during the test. These forces are measured by sensors and electrical outputs of transducer 36 can be sent to suitable circuitry and analyzed by a microprocessor 99, to provide the friction angle. The microprocessor also can operate the motor 84, through controls 100, which can also be manually operated.

The measurement of forces also allows for monitoring the sharpness of a sharp cutter. If the cutter is sharp, then $$\frac{F_n}{F_s} = \xi$$

where the constant $\xi$ is related to the cutter rake angle $\theta$ and the interfacial friction angle $\psi$ on the cutting face by:

$$= \tan(\theta + \psi)$$

The rake angle $\theta$ of a sharp cutter is typically 15° and interfacial friction angle $\psi$ has been determined to be about 19°, independently of the rock being cut. Hence $\xi = 0.67$. A sharp cutter has thus lost its sharpness if $F_n/F_s > \xi$. Realistically, one will consider the cutter to be blunt if $\xi > 0.75$. ($F_n/F_s > 0.75$)

The interpretation of the force measurements $F_n$ and $F_s$ in terms of rock strength parameters is possible only if the mode of destruction of the rock is plastic. In sedimentary rocks (sandstones, limestones, shales, chalk, etc.), this mode of rock destruction takes place for depth of cut typically smaller than 2 to 3 mm. Larger depths of cut will cause chipping of the rock, which is associated with a brittle mode of failure. As stated, the preferred range of depth for the direct measurement of friction angle is 0.05 to 0.1 mm.

A sharp cutter can be used in the present portable test device to measure cohesion. A sharp cutter has an edge that engages a rock and the cohesion is a measure of $F_s$ (horizontal force) divided by the area of the cut on the sample, that is the depth of the cut by the width of the cutter.

While moving the rock sample relative to the cutter is shown, the cutter also can be moved relative to a stationary sample so long as rigidity is maintained and constant speed is achieved.

In prior methods of determining friction angle several cuts with a blunt cutter at different depths of cut are made and an analysis of the results as shown in U.S. Pat. No. 5,216,917 can be carried out and leads to the determination of function angle. The same prior methods also can be used with the present tester, if desired.

Although the present invention has been described with reference to preferred embodiments, workers skilled in the art will recognize that changes may be made in form and detail without departing from the spirit and scope of the invention.

What is claimed is:

1. A rock strength evaluation device including a frame, a cutter support on the frame, having a cutter thereon, a rock sample support on the frame, at least one of the cutter support and rock sample support being movable in a displacement direction relative to the other with the cutter engaging a rock sample on the rock sample support, the cutter having a flat face trailing an edge defined by a surface of the cutter first engaging a rock sample as relative movement occurs and the flat face, the flat face forming a shallow angle inclined upwardly toward the edge to cause rock from the rock sample to form a boundary layer of powdered rock as relative displacement occurs.

2. The device of claim 1, wherein the shallow angle is no more than 4°.

3. The device of claim 1, wherein the shallow angle is 2°.

4. The device of claim 1, wherein the depth of the cut made by the cutter is less than 3 mm.

5. The device of claim 4, where the depth of cut is between 0.05 and 0.1 mm.

6. The device of claim 4 and a drive to cause the displacement to occur at a constant velocity.

7. The device of claim 6, wherein the constant velocity is in the range of 1 cm/sec.

8. The device of claim 1 including a support for the cutter including sensors to individually sense forces exerted on the cutter during displacement in direction parallel to a direction of displacement ($F_s$) and normal to the direction of displacement ($F_n$).

9. A portable rock strength evaluation device including a rigid self-support frame, a cutter support on the frame having a cutter thereon, a rock sample support on the frame, at least one of the supports being movable in a displacement direction relative to the other with the cutter engaging a rock sample on the rock sample support, the cutter engaging a rock sample as relative movement occurs, to cut a portion of rock from the sample, a transducer supporting the cutter on the frame and measuring forces normal to the displacement direction ($F_n$) and separately parallel to the displacement direction ($F_s$), and means to provide the quantity $\tan\phi = F_s/F_n$ where $\phi$ is the internal friction angle.

* * * * *